United States Patent
Fukumoto

(10) Patent No.: US 8,550,999 B2
(45) Date of Patent: Oct. 8, 2013

(54) ULTRASOUND DIAGNOSTIC APPARATUS

(75) Inventor: Takenori Fukumoto, Kanagawa (JP)

(73) Assignee: Panasonic Corporation, Osaka (JP)

( * ) Notice: Subject to any disclaimer, the term of this patent is extended or adjusted under 35 U.S.C. 154(b) by 127 days.

(21) Appl. No.: 12/999,357

(22) PCT Filed: Jun. 26, 2009

(86) PCT No.: PCT/JP2009/002954
§ 371 (c)(1),
(2), (4) Date: Dec. 16, 2010

(87) PCT Pub. No.: WO2010/001564
PCT Pub. Date: Jan. 7, 2010

(65) Prior Publication Data
US 2011/0096958 A1 Apr. 28, 2011

(30) Foreign Application Priority Data

Jul. 1, 2008 (JP) .................................. 2008-172439

(51) Int. Cl.
*A61B 8/00* (2006.01)
(52) U.S. Cl.
USPC ............................ 600/438; 600/407; 600/437
(58) Field of Classification Search
USPC ....................................................... 600/438
See application file for complete search history.

(56) References Cited

U.S. PATENT DOCUMENTS

2006/0058649 A1 3/2006 Tamano et al.
2008/0081993 A1* 4/2008 Waki .............................. 600/438

FOREIGN PATENT DOCUMENTS

| JP | 59-060378 A | 4/1984 |
| JP | 2507383 B | 4/1996 |
| JP | 2000-229078 A | 8/2000 |
| JP | 2003-225238 A | 8/2003 |
| JP | 2006-181052 A | 7/2006 |
| JP | 2006-230618 A | 9/2006 |
| JP | 2008-272308 A | 11/2008 |

OTHER PUBLICATIONS

International Search Report for corresponding International Application No. PCT/JP2009/002954 mailed Jul. 28, 2009.
Kanai et al., "Inner Vision", 20.9, pp. 31-33, 2005 and concise English explanation.

\* cited by examiner

*Primary Examiner* — Unsu Jung
*Assistant Examiner* — Saurel J Selkin
(74) *Attorney, Agent, or Firm* — Renner, Otto, Boisselle & Sklar, LLP

(57) ABSTRACT

An ultrasonic diagnostic apparatus includes: a transmitting section for generating first, second and third drive signals to drive an ultrasonic probe; a receiving section for getting echoes, produced by reflection of the ultrasonic waves responsive to those drive signals and generating first, second and third received echo signals; a storage section to store the first received echo signal; an adjusting section for defining intense and faint echo regions within a measuring range for the first received echo signal based on a stored feature quantity and for determining the second and third gains based on the feature quantities in the intense and faint echo regions; a displacement measuring section for measuring the magnitudes of displacement in the echo regions based on the second and third received echo signals; and a qualitative value calculating section for calculating the attribute property value of the subject based on the magnitudes of displacement.

31 Claims, 12 Drawing Sheets

FIG.2
(a)
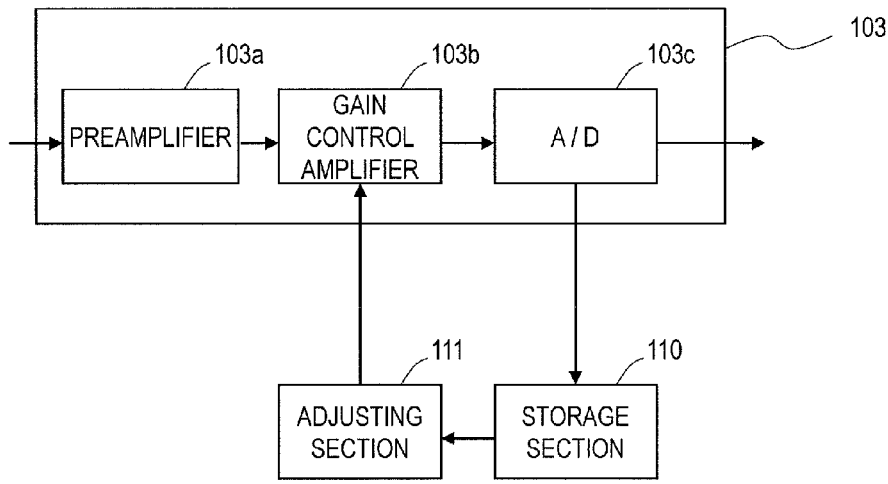
(b)
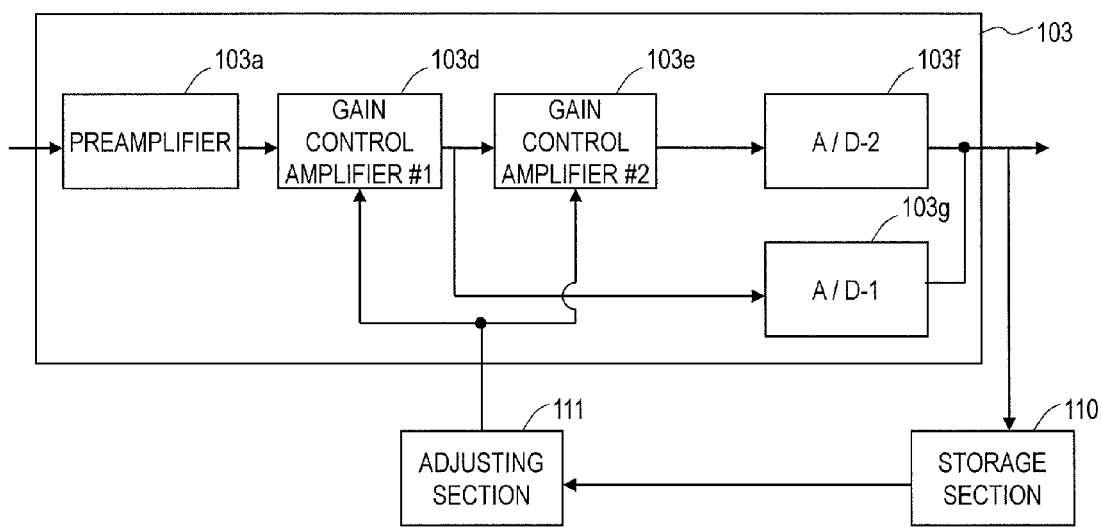

FIG.3
(a)
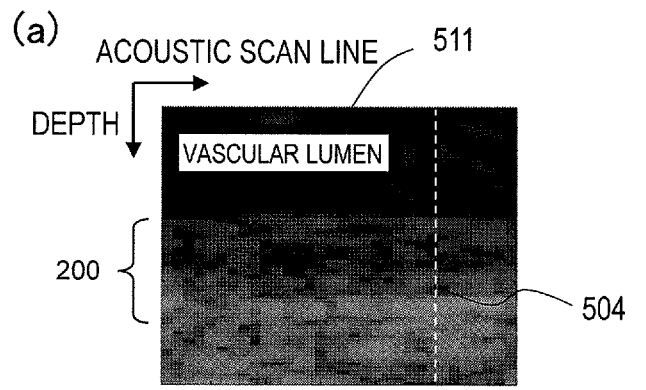
(b)
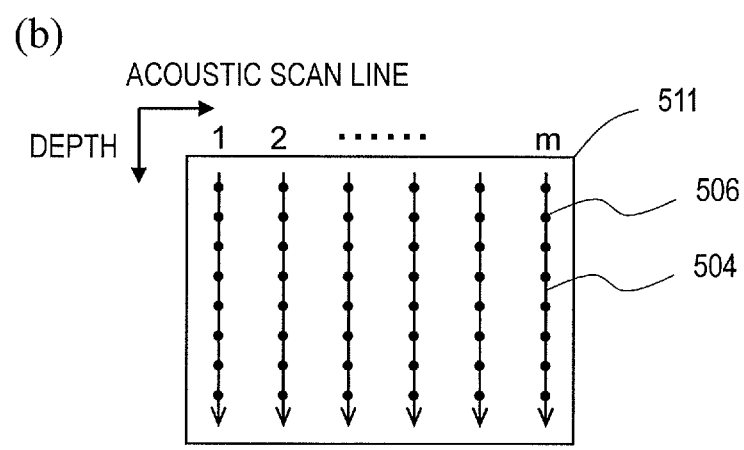
(c)
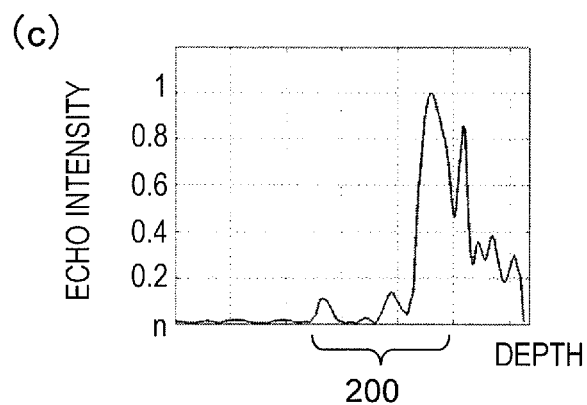

FIG. 7
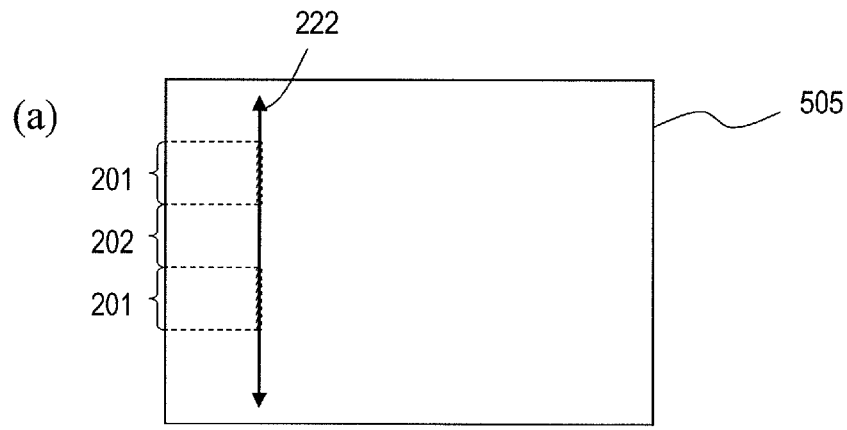
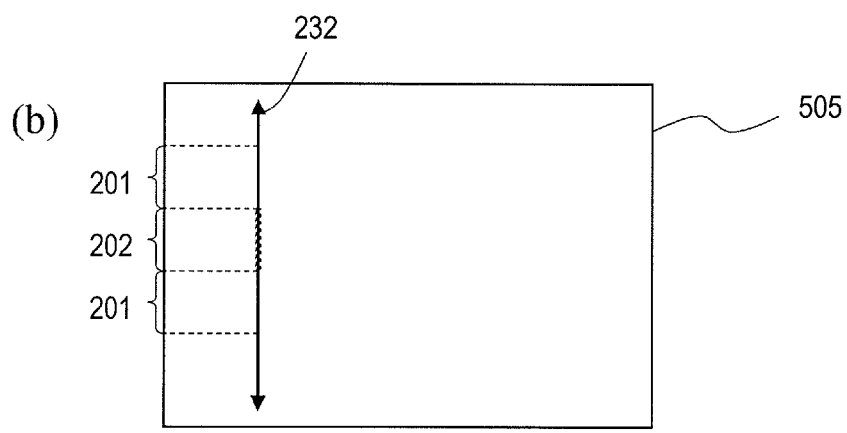
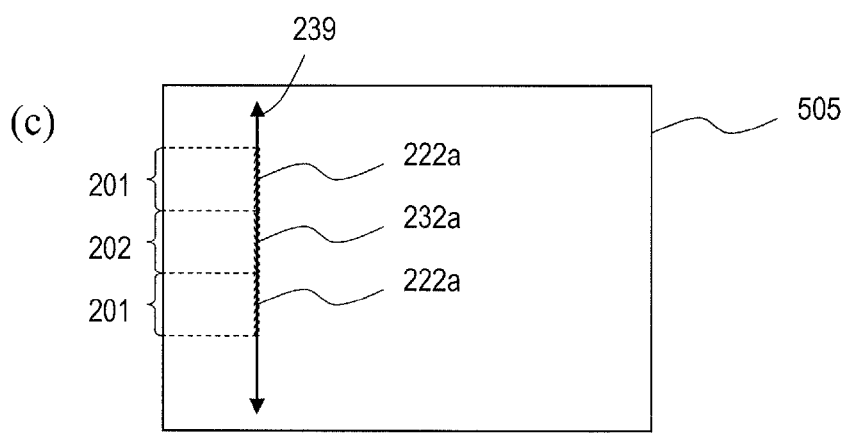

FIG. 12
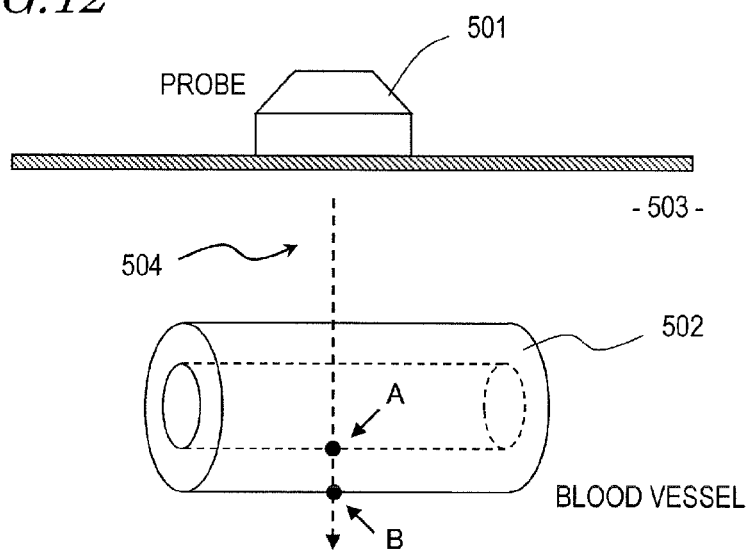
(a)
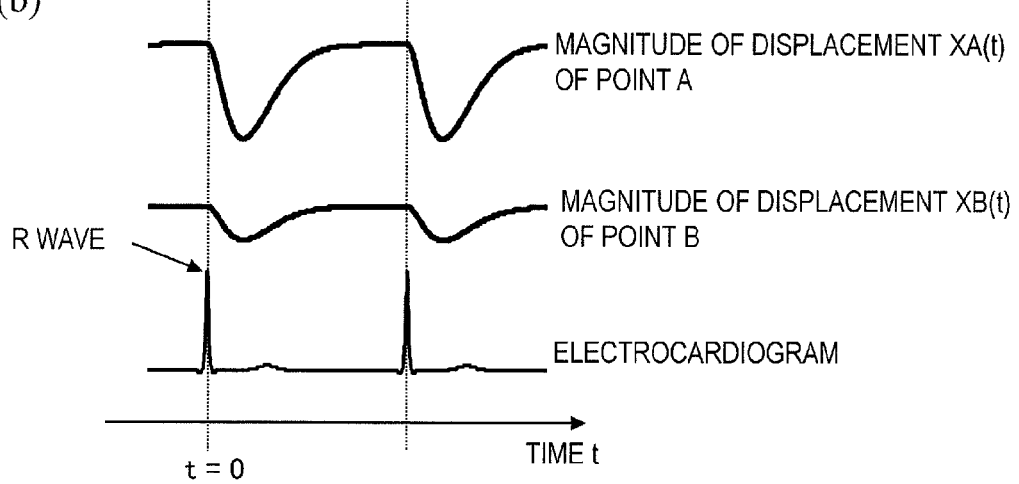
(b)

ULTRASOUND DIAGNOSTIC APPARATUS

TECHNICAL FIELD

The present invention relates to an ultrasonic diagnostic apparatus for measuring the subject's tissue attribute.

BACKGROUND ART

An ultrasonic diagnostic apparatus obtains biological information from a subject by irradiating him or her with an ultrasonic wave and analyzing the information contained in its echo signal. For example, a conventional ultrasonic diagnostic apparatus that has been used extensively converts the intensity of the echo signal into its associated pixel luminance, thereby presenting the subject's internal structure as a tomographic image. In this manner, the internal structure of the subject can be known.

Some people are attempting recently to track the motion of a subject's tissue and evaluate the strain and the elasticity, viscosity or any other attribute property of the tissue mainly by analyzing the amplitude or phase information of the echo signal. For example, Patent Document No. 1 and Non-Patent Document No. 1 disclose a method for obtaining the magnitude of strain based on the magnitude of displacement of a measuring point that has been set on the vascular wall due to the heartbeat and calculating the local elasticity around the measuring point based on the magnitude of the strain and the blood pressure difference and also disclose a method for presenting the spatial distribution of elasticities as an image. Hereinafter, these methods will be described.

The arterial vascular wall will be deformed due to a variation in blood pressure that has been caused by the heartbeat. Based on the relation between the degree of that deformation (i.e., the magnitude of strain) and the stress produced by the blood pressure in the arterial vascular wall, the elasticity of the vascular wall can be defined. In this case, it is difficult to measure noninvasively, or estimate indirectly, the distribution of stress in the arterial vascular wall. For that reason, the magnitude of strain ϵ of the arterial vascular wall during one heartbeat is measured with ultrasonic waves. And based on the difference between the lowest and highest blood pressures Pd and Ps that have been measured separately with a blood pressure manometer (i.e., based on the pulse $\Delta P = Ps - Pd$), the elasticity E of the arterial vascular wall is defined by the following Equation (1):

$$E = \frac{\Delta P}{\varepsilon} \tag{1}$$

Using ultrasonic waves, the magnitude of strain may be measured in the following manner:

First of all, points A and B are set on the intima and adventitia of the vascular wall of the artery 502 of the subject 503 as shown in FIG. 12(a). Suppose an ultrasonic beam 504 has been sent from a probe 501 to obtain an echo signal and the magnitude of strain ϵ of the vascular wall between those two points is calculated based on that echo signal.

The positions of those two points at a point in time t are identified by XA(t) and XB(t), respectively, and a time t=0 is set using the R wave of the electrocardiogram at the end of the diastole as a trigger. FIG. 12(b) shows exemplary waveforms of XA(t) and XB(t). After t=0, XA(t) and XB(t) both decrease because the blood vessel shrinks.

The initial thickness $h_0$ is calculated by $h_0 = XB(0) - XA(0)$ and the greatest thickness difference $\Delta h$ is represented by the following Equation (2):

$$\Delta h = \mathrm{MAX}[|XB(t) - XA(t)|] \tag{2}$$

The magnitude of strain ϵ is given by the following Equation (3):

$$\varepsilon = \frac{\Delta h}{h_0} = \frac{\mathrm{MAX}[|XB(t) - XA(t)|]}{XB(0) - XA(0)} \tag{3}$$

where MAX [*] is a function representing the maximum value of *.

Generally speaking, the displacement of the arterial vascular wall due to the dilation or shrinkage of the artery is on the order of several hundred μm, while the greatest thickness difference Δh of the vascular wall is on the order of several ten μm. Thus, the variation in thickness, which is approximately one digit smaller than the wavelength of the ultrasonic waves for use to make measurement (e.g., about 300 μm), should be sensed accurately.

In the example described above, the magnitude of strain ϵ is supposed to be calculated between two points on the intima and adventitia sides of the vascular wall. On the other hand, according to the methods disclosed in Patent Document No. 1 and Non-Patent Document No. 1, a number of displacement measuring points are set at intervals of approximately 80 μm on each ultrasonic beam 504 within the measuring range 510 and the magnitude of displacement is measured at each of those measuring points as shown in FIG. 13. The ultrasonic wave for use to make measurement has a pulse width of approximately 400 μm. That is why two measuring points are set so that the initial thickness $h_0$ calculated by Equation (1) becomes approximately 400 μm, the greatest thickness difference Δh is calculated by Equation (2) on the supposition that the thickness variation is constant between those two points, and Δh is supposed to be the greatest thickness difference at the midpoint between those two points. While vertically shifting that layer from the intima side of the vascular wall toward its adventitia side by the interval between each pair of measuring points each time, Δh is calculated with respect to each measuring point. Furthermore, by scanning the blood vessel 502 with the ultrasonic beam 504 along its length at intervals of several hundred μm, thousands of very small regions are defied in the axial and depth directions of the vascular wall and Δh is calculated in each of those very small regions. The magnitude of strain ϵ in each very small region is calculated based on h and Δh thus obtained, and the elasticity E of each very small region 511 is obtained by Equation (1) based on the pulse ΔP that has been measured separately with a blood pressure manometer.

CITATION LIST

Patent Literature

Patent Document No. 1: Japanese Patent Application Laid-Open Publication No. 2000-229078
Patent Document No. 2: Japanese Patent No. 2507383
Patent Document No. 3: Japanese Patent Application Laid-Open Publication No. 2006-230618

Non-Patent Literature

Non-Patent Document No. 1: Kanai et al., Inner Vision 20.9, pp. 31-33, 2005

SUMMARY OF INVENTION

Technical Problem

To measure the magnitude of displacement at each measuring point accurately by the method described above, the echo signal obtained from each measuring point should have a high SNR. In other words, the amplitude of the echo signal obtained from each measuring point needs to be large enough and non-saturated.

Various receivers are often equipped with an automatic gain controller (AGC) to keep the intensity of the received signal constant. However, the AGC is supposed to be applied to a continuous signal such as a TV video signal. That is why if the known AGC were used in the ultrasonic diagnostic apparatus disclosed in Patent Document No. 1 or Non-Patent Document No. 1, the received signal would get saturated where the intensity of the echo signal changes from a low intensity range into a high intensity range.

To overcome such a problem, Patent Document No. 2 discloses a receiver for an ultrasonic flaw detector, which gets the peak of the echo signal obtained from the object detected by a time gate circuit and which controls the gain so as to maximize that peak. However, if such a technique were applied to the ultrasonic diagnostic apparatus disclosed in Patent Document No. 1 or Non-Patent Document No. 1, the gain would vary while an echo that forms one acoustic line is being received and the displacement of the measuring point could not be measured accurately. That is a problem.

Patent Document No. 3 discloses a technique for controlling at least one of the gain of an echo signal received and the intensity of an ultrasonic wave signal to be sent toward the subject based on the maximum value of that echo signal and synchronously with the deformation period of the subject. In general, however, the intensity of an echo signal that has come from a vital tissue will vary significantly according to the structure of that target tissue. That is why if an acoustic scan line is set perpendicularly to the axis of the artery, an ultrasonic wave is sent, and then an echo signal is received, then the SNR of the echo signal would be quite different depending on whether the echo signal has come from the vicinity of the blood flow-intima boundary or the media-adventitia boundary, where the echo signal has a very high intensity, or from an intima-media range or its surrounding tissue where the echo signal has a very low intensity. As a result, the accuracy of displacement measurement within the target measuring range would vary significantly.

It is therefore an object of the present invention to provide an ultrasonic diagnostic apparatus that can measure the subject's attribute property accurately.

Solution to Problem

An ultrasonic diagnostic apparatus according to the present invention includes: a transmitting section for generating N different drive signals (where N is an integer that is equal to or greater than three), including a first drive signal, to drive a probe that sends out ultrasonic waves toward a subject; a receiving section for getting echoes, which have been produced as a result of reflection of the ultrasonic waves from the subject in response to the N different drive signals, received by the probe and amplifying the respective signals generated, thereby generating a first received signal that responds to the first drive signal and N−1 received echo signals; a storage section to store the first received echo signal; an adjusting section for defining M different echo regions (where M is an integer that falls within the range of two through N−1) within a measuring range on the acoustic line of the first received echo signal based on a feature quantity of the first received echo signal that is stored in the storage section and for determining either the amplification gain to generate the N−1 received echo signals in the receiving section or the waveforms of the N−1 different drive signals, except the first drive signal, based on the feature quantities of the first received echo signal in the M different echo regions; a displacement measuring section for measuring the respective magnitudes of displacement in the M different echo regions based on the N−1 received echo signals; and a qualitative value calculating section for calculating the attribute property value of the subject within the measuring range based on the respective magnitudes of displacement in the M different echo regions.

In one preferred embodiment, N−1 and M are both equal to two. The M different echo regions are an intense echo region in which the echo signal has a relatively high intensity and a faint echo region in which the echo signal has a relatively low intensity. The transmitting section generates not only the first drive signal but also second and third drive signals as well. The receiving section gets echoes, which have been produced as a result of reflection of the ultrasonic waves from the subject in response to the first, second and third drive signals, received by the probe and amplifies the respective signals generated with first, second and third gains, respectively, thereby generating the first received echo signal and second and third received echo signals. The adjusting section defines the intense and faint echo regions within the measuring range on the acoustic line of the first received echo signal based on the feature quantity of the first received echo signal that is stored in the storage section and determines the second and third gains based on the feature quantities of the first received echo signal in the intense and faint echo regions. The displacement measuring section measures the respective magnitudes of displacement in the intense and faint echo regions based on the second and third received echo signals, respectively. The qualitative value calculating section calculates the attribute property value of the subject within the measuring range based on the respective magnitudes of displacement in the intense and faint echo regions.

In an alternative preferred embodiment, N−1 and M are both equal to two. The M different echo regions are an intense echo region in which the echo signal has a relatively high intensity and a faint echo region in which the echo signal has a relatively low intensity. The transmitting section generates not only the first drive signal but also second and third drive signals as well. The receiving section gets echoes, which have been produced as a result of reflection of the ultrasonic waves from the subject in response to the first, second and third drive signals, received by the probe and amplifies the respective signals generated, thereby generating the first received echo signal and second and third received echo signals. The adjusting section defines the intense and faint echo regions within the measuring range on the acoustic line of the first received echo signal based on the feature quantity of the first received echo signal that is stored in the storage section and determines the waveforms of the second and third drive signals in the transmitting section based on the feature quantities of the first received echo signal in the intense and faint echo regions. The displacement measuring section measures the respective magnitudes of displacement in the intense and faint echo regions based on the second and third received echo signals, respectively. The qualitative value calculating section calculates the attribute property value of the subject within the measuring range based on the respective magnitudes of displacement in the intense and faint echo regions.

In one preferred embodiment, the adjusting section keeps the second and third gains constant within the same deformation period of the subject.

In another preferred embodiment, the adjusting section keeps the waveforms of the second and third drive signals constant through the same deformation period of the subject.

In still another preferred embodiment, the feature quantity of the first received echo signal is the amplitude of the first received echo signal.

In yet another preferred embodiment, the adjusting section determines the second and third gains by the amplitude value of the first received echo signal so that the amplitudes of the second and third received echo signals in the intense and faint echo regions fall within a predetermined range.

In yet another preferred embodiment, the adjusting section determines the waveforms of the second and third drive signals by the amplitude value of the first received echo signal so that the amplitudes of the second and third received echo signals in the intense and faint echo regions fall within a predetermined range.

In yet another preferred embodiment, the adjusting section defines a region in which the amplitude of the first received echo signal is equal to or greater than a predetermined threshold value to be the intense echo region.

In yet another preferred embodiment, the adjusting section defines a region in which the amplitude of the first received echo signal is smaller than the predetermined threshold value to be the faint echo region.

In yet another preferred embodiment, the threshold value is determined by the maximum amplitude of the first received echo signal.

In yet another preferred embodiment, the threshold value is determined by the average amplitude of the first received echo signal.

In yet another preferred embodiment, the threshold value is determined by the average amplitude and standard deviation of the first received echo signal.

In yet another preferred embodiment, the adjusting section determines the gains for the intense and faint echo regions by the amplitude value of the first received echo signal so that the maximum amplitudes of the second and third received echo signals in the intense and faint echo regions, respectively, fall within a predetermined range.

In yet another preferred embodiment, the adjusting section determines the waveforms of the second and third drive signals by the amplitude value of the first echo signal so that the maximum amplitudes of the second and third received echo signals in the intense and faint echo regions, respectively, fall within a predetermined range.

In yet another preferred embodiment, the adjusting section determines the gains for the intense and faint echo regions synchronously with one cardiac cycle of the subject.

In yet another preferred embodiment, the adjusting section determines the waveforms of the second and third drive signals synchronously with one cardiac cycle of the subject.

In yet another preferred embodiment, the adjusting section receives information about the cardiac cycle from either an electrocardiograph or phonocardiograph that is connected to the subject.

In yet another preferred embodiment, at least a portion of the subject is deformed periodically by a vibrator and the adjusting section receives information about the period of deformation from the vibrator.

In yet another preferred embodiment, the adjusting section adjusts the amplitude value of the drive signal.

In yet another preferred embodiment, the attribute property is the magnitude of strain.

In yet another preferred embodiment, the attribute property is the modulus of elasticity.

In yet another preferred embodiment, multiple acoustic lines are set on the subject and the transmitting section generates the first, second and third drive signals so that the ultrasonic waves scan the subject on their associated acoustic lines. The receiving section generates multiple sets of first, second and third received echo signals on the multiple acoustic lines. And the storage section stores the respective first received echo signals of the multiple sets.

Advantageous Effects of Invention

According to the present invention, intense and faint echo regions, in which the received echo signal has relatively high and relatively low signal intensities, are defined within a measuring range on the subject by using the first received echo signal responsive to the first drive signal, and the second and third gains are determined based on the feature quantity about the signal intensities of the first received echo signal in the intense and faint echo regions. The second and third received echo signals, which have been amplified with the second and third gains determined, can be maximized as far as the signal intensities in the intense and faint echo regions are not saturated. As a result, a received echo signal with a high SNR can be used and almost equally accurate results of measurement can be obtained over the entire measuring range.

BRIEF DESCRIPTION OF DRAWINGS

FIGS. 2($a$) and 2($b$) are block diagrams illustrating two different configurations for the receiving section.

FIG. 3($a$) shows an example of a tomographic image taken by the ultrasonic diagnostic apparatus shown in FIG. 1, FIG. 3($b$) schematically illustrates an ultrasonic wave to scan the measuring range and displacement measuring points that are set on its acoustic lines, and FIG. 3($c$) shows the signal intensity of a received echo signal obtained on an acoustic line.

Figure 4:
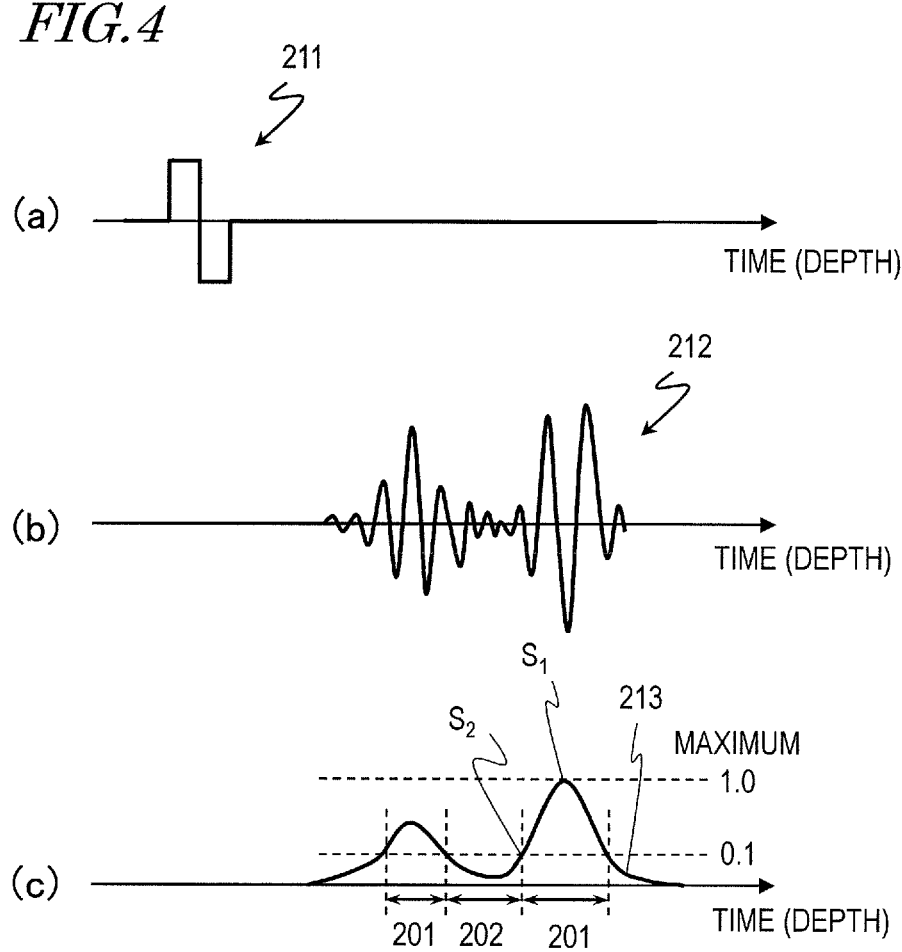

Portions (a), (b) and (c) of FIG. 4 show the waveform of a first drive signal, the waveform of a first received echo signal, and the signal intensity curve of the first received echo signal, respectively.

Figure 5:
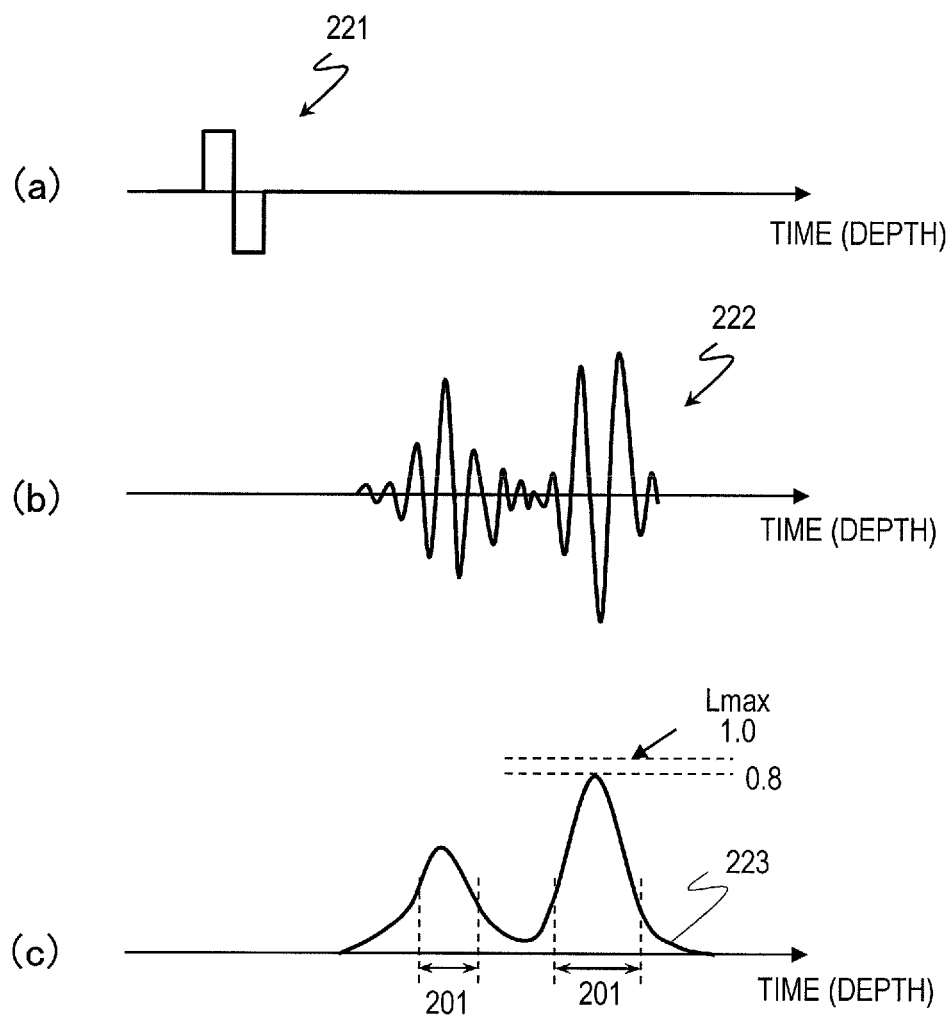

Portions (a), (b) and (c) of FIG. 5 show the waveform of a second drive signal, the waveform of a second received echo signal, and the signal intensity curve of the second received echo signal, respectively.

Figure 6:
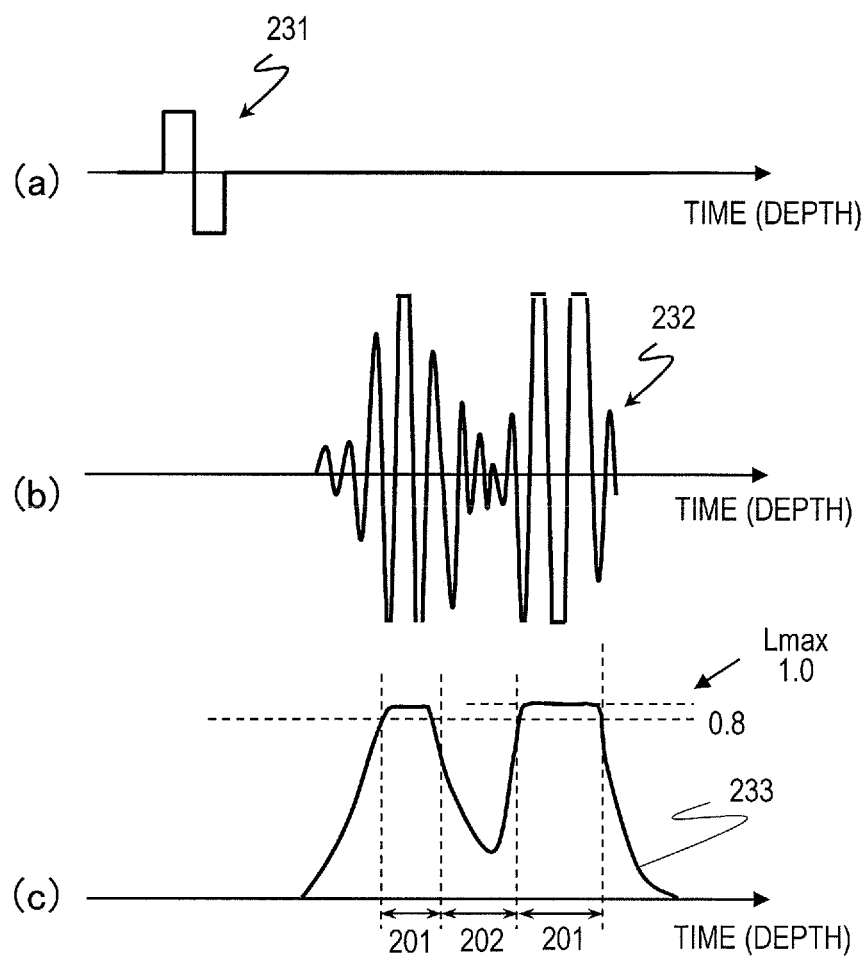

Portions (a), (b) and (c) of FIG. 6 show the waveform of a third drive signal, the waveform of a third received echo signal, and the signal intensity curve of the third received echo signal, respectively.

FIGS. 7($a$) to 7($c$) schematically show the relation between intense and faint echo regions and the second and third received echo signals.

Figure 8:
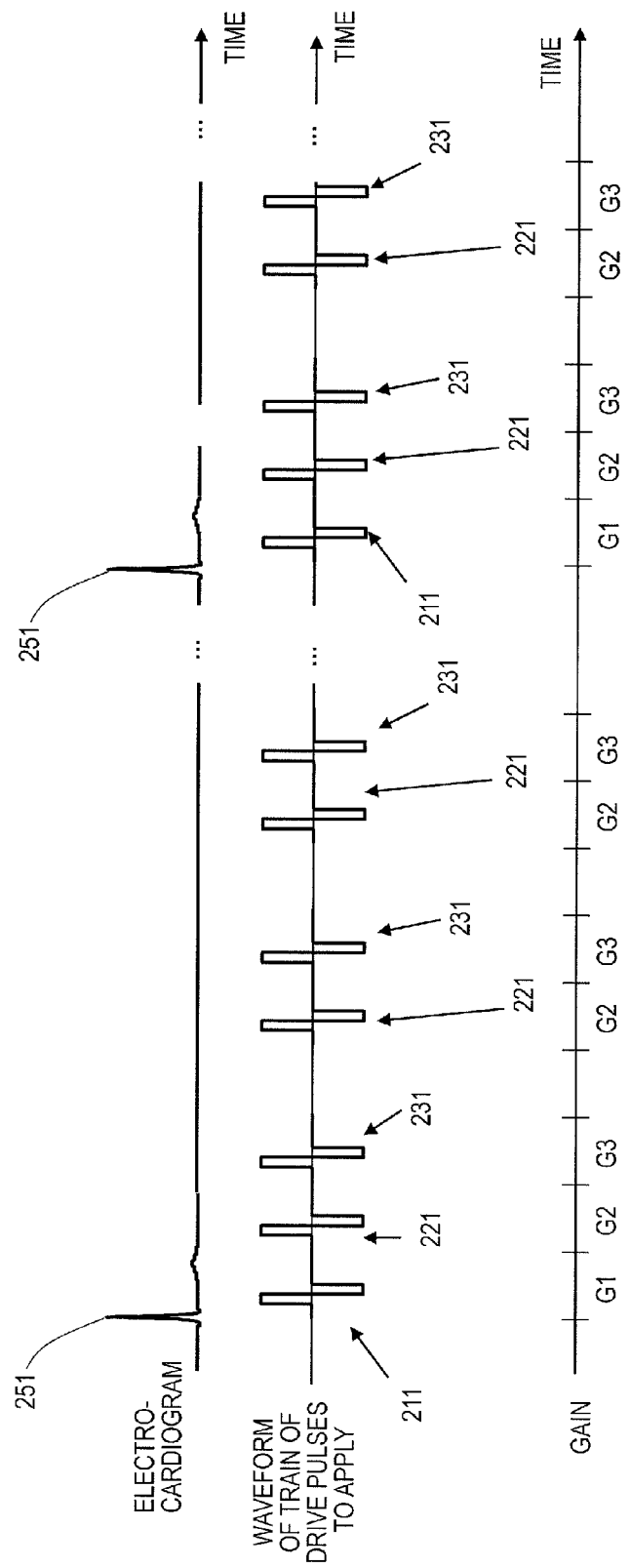

FIG. 8 is a timing diagram showing the relation between a transmitted drive signal and its associated gains.

Figure 9:
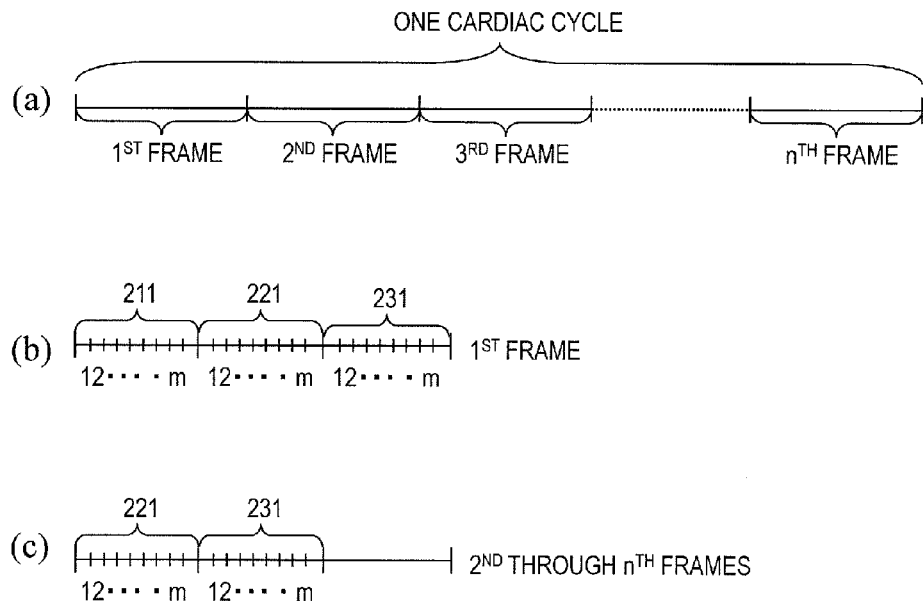

FIGS. 9($a$) to 9($c$) schematically indicate the timings to apply the first, second and third drive signals when the measuring range is scanned.

Figure 10:
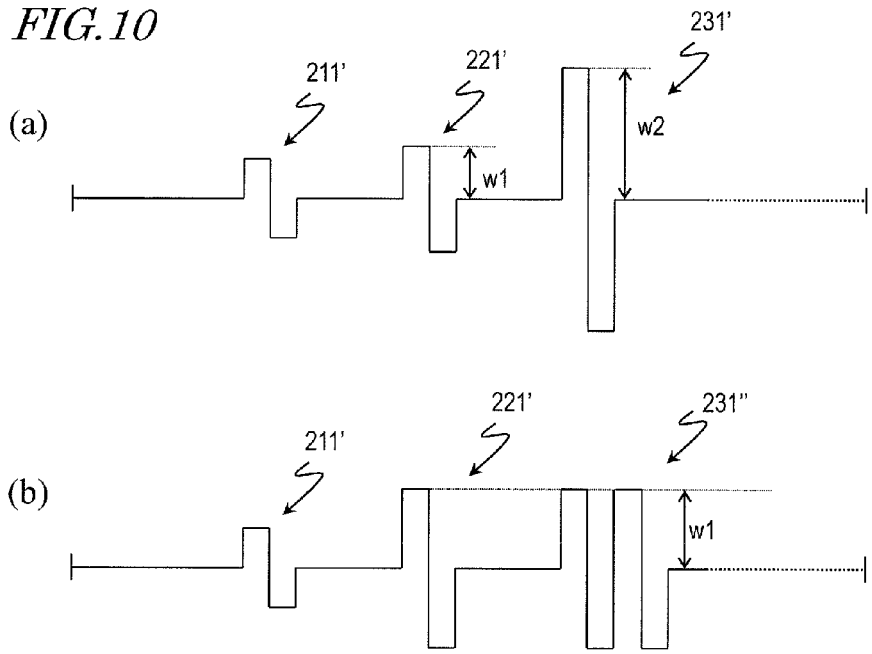

Portions (a) and (b) of FIG. 10 show exemplary waveforms for use in a situation where the drive signal needs to be adjusted.

Figure 11:
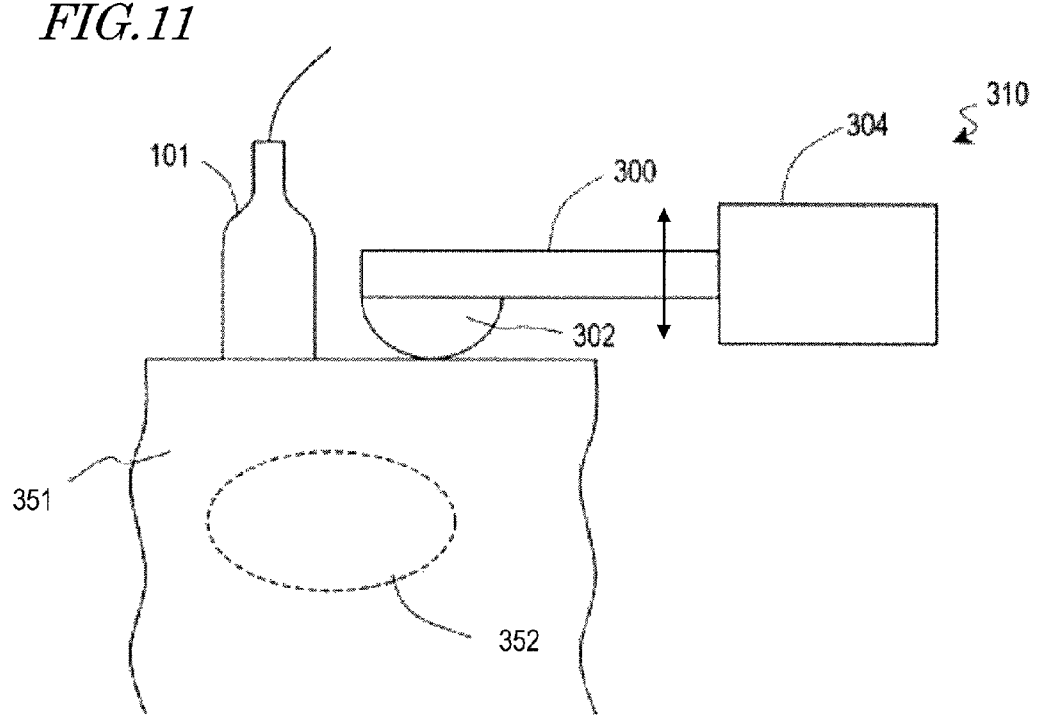

FIG. 11 is a schematic representation illustrating an arrangement for estimating the elasticity of a resting organ.

FIG. 12(a) is a schematic representation illustrating how to obtain waveforms representing the magnitudes of displacement at two displacement measuring points on a vascular wall, and FIG. 12(b) shows examples of displacement waveforms thus obtained.

Figure 13:
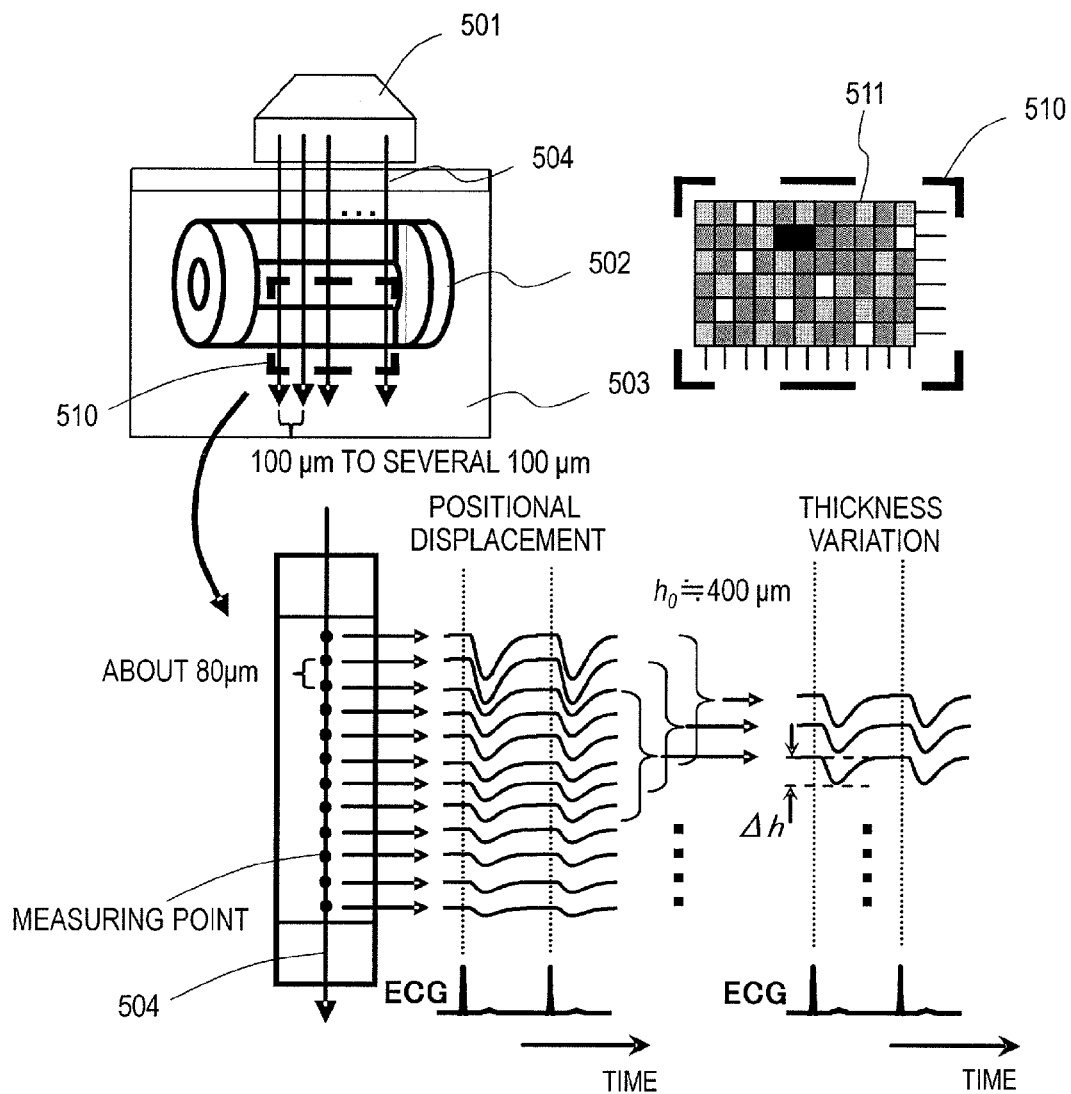

FIG. 13 is a schematic representation illustrating a conventional method for measuring elasticity.

DESCRIPTION OF EMBODIMENTS

Hereinafter, preferred embodiments of the present invention will be described with reference to the accompanying drawings.

Figure 1:
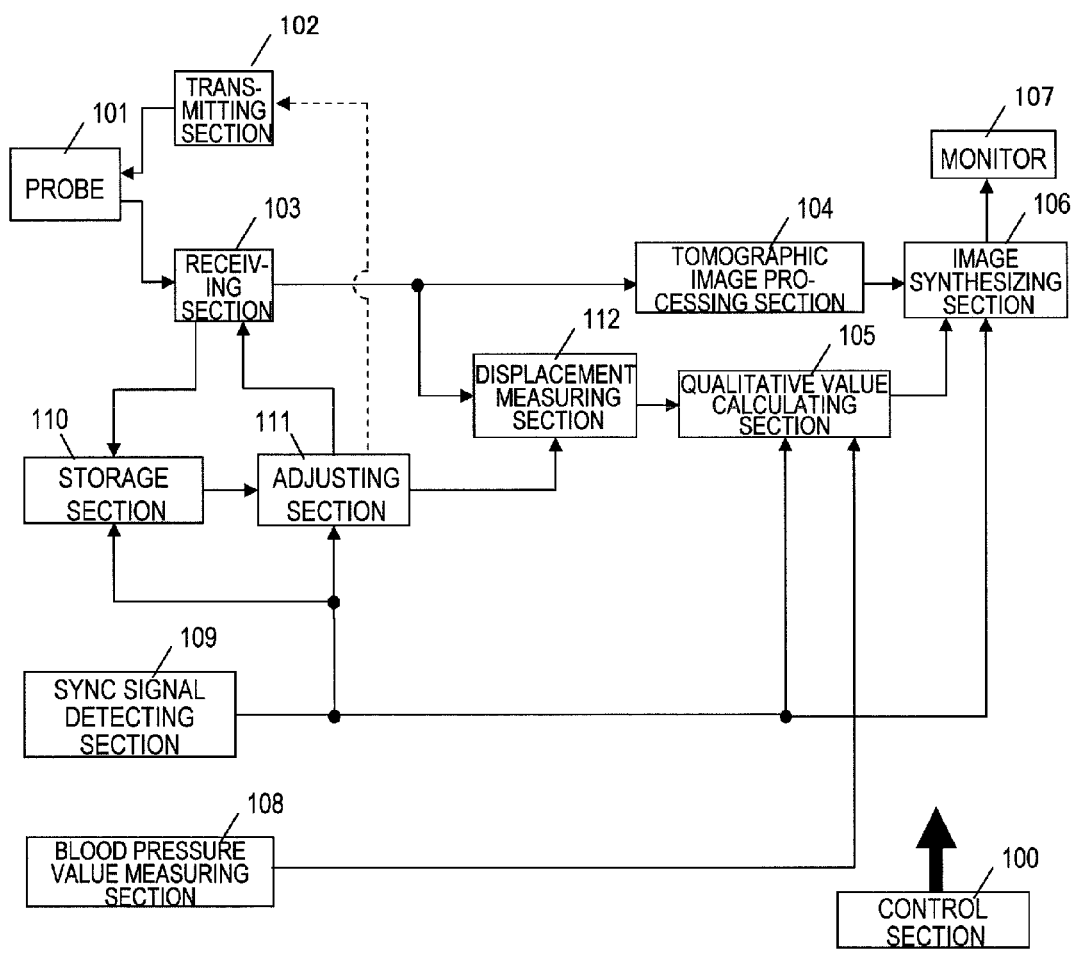
FIG. 1 is a block diagram illustrating a preferred embodiment of an ultrasonic diagnostic apparatus according to the present invention.

FIG. 1 is a block diagram illustrating a preferred embodiment of an ultrasonic diagnostic apparatus according to the present invention. The ultrasonic diagnostic apparatus of this preferred embodiment measures either a shape property or an attribute property of the subject. Particularly if the subject is an organism, the present invention can be used effectively to measure the elasticity of its arterial vascular wall tissue. In the following description, a preferred embodiment of the present invention will be described as being applied to measuring the attribute property value of the arterial vascular wall tissue of the subject. The artery is deformed so as to dilate and shrink periodically at regular intervals as the heart pumps out blood.

As shown in FIG. 1, the ultrasonic diagnostic apparatus of this preferred embodiment includes a transmitting section 102, a receiving section 103, a tomographic image processing section 104, a qualitative value calculating section 105, an image synthesizing section 106, a storage section 110, an adjusting section 111, and a displacement measuring section 112. The apparatus further includes a control section 100 for controlling all of these circuit sections. Although not shown, a user interface such as a keyboard, a track ball, a switch or a button is connected to the control section 100. And when the user enters his or her command into the control section 100 through the user interface, the control section 100 controls the respective sections of the ultrasonic diagnostic apparatus. The control section 100 may be implemented as a microcomputer, for example. The functions of the qualitative value calculating section 105, the image synthesizing section 106, the storage section 110, the adjusting section 111 and the displacement measuring section 112 to be described later may be performed by software, too.

A probe 101 and a monitor 107 are connected to the ultrasonic diagnostic apparatus. A general purpose probe may be used as the probe 101. Or the ultrasonic diagnostic apparatus of this preferred embodiment may include the probe 101 by itself. To obtain a two-dimensional distribution of attribute property values of the arterial vascular wall tissue, the probe 101 is preferably a two- or three-dimensional array of probes. Anything may be used as the monitor 107 as long as it can display the results of measurements thereon.

A blood pressure value measuring section 108 and a sync signal detector 109 are further connected to the ultrasonic diagnostic apparatus. The blood pressure value measuring section 108 may be a blood pressure manometer, for example, and measures the highest and lowest blood pressures of the subject and outputs them to the ultrasonic diagnostic apparatus. The sync signal detector 109 may be an electrocardiograph, for example, and outputs a signal to the ultrasonic diagnostic apparatus synchronously with one cardiac cycle. As will be described in detail later, an R wave of the electrocardiogram obtained from the subject may be output to the ultrasonic diagnostic apparatus.

Under the control of the control section 100, the transmitting section 102 generates a drive signal to drive the probe 101 that sends out an ultrasonic wave to the subject. As will be described in detail later, the transmitting section 102 generates first, second and third drive signals for mutually different purposes and outputs them to the probe 101. Each of these drive signals includes multiple pulse signals.

According to the present invention, in a received echo signal that has been obtained on the same acoustic line, its gain is changed between a faint echo region and an intense echo region thereof. If the gain values were changed halfway through a single received echo signal, then the magnitude of displacement measured would be inaccurate as described above. For that reason, two drive signals, which will be referred to herein as second and third drive signals, respectively, are used. Meanwhile, the first drive signal is used to determine whether some part of the measuring range on the acoustic line is an intense echo region or a faint echo region. These drive signals will be described in detail later.

The probe 101 includes a number of piezoelectric vibrators, each of which vibrates and produces an ultrasonic wave responsive to the drive signal applied thereto. More specifically, in response to the first, second and third drive signals applied by the transmitting section 102, three ultrasonic waves are produced and sent out toward the subject. The ultrasonic wave that has been reflected from the subject returns as an echo to the probe 101, which converts the received echo into an electrical signal and generates first, second and third detection signals.

As shown in FIG. 2(a), the receiving section 103 may include a preamplifier 103a, a gain control amplifier 103b and an A/D converter 103c, for example. The preamplifier 103a amplifies the first, second and third detection signals, which have been received from the probe 101, with a predetermined gain, thereby generating first, second and third received echo signals, respectively. In accordance with a control signal supplied from the adjusting section 111, the gain control amplifier 103b can vary the gain. More specifically, in accordance with the control signal supplied from the adjusting section 111, the gain control amplifier 103b amplifies the first, second and third detection signals with first, second and third gains, respectively. The first, second and third received echo signals thus obtained are output to the A/D converter 103c and converted into digital signals there. Although not shown in FIG. 1 or 2(a), the receiving section 103 further includes a beam former, which controls the respective time delays caused by the piezoelectric vibrators of the probe 101. As a result, the signals representing the echoes that have been detected by the piezoelectric vibrators of the probe 101 are synthesized together so as to be a reflected wave that has come from a predetermined direction before being input to the preamplifier 103a.

According to this preferred embodiment, to obtain a qualitative value, the received echo signals are digitized by the A/D converter 103c. That is why the upper limit of the A/D conversion dynamic range of the A/D converter 103c becomes the saturation level of the received echo signals. Nevertheless, the A/D converter is not an indispensable element according to the present invention. Even if the received echo signals are processed as they are as analog signals, there will also be an upper limit to the signal processing amplitude and that upper limit should be the saturation level of the received echo signals.

The storage section 110 stores the first received echo signal that has been digitized. By reference to the feature quantity of the first received echo signal that is stored in the storage section 110 (particularly the feature quantity about the signal intensity), the adjusting section 111 determines an intense echo region with a relatively high signal intensity and a faint echo region with a relatively low signal intensity in the measuring range on the acoustic line of the first received echo signal. In addition, based on the feature quantities about the signal intensities of the first received echo signal in the intense and faint echo regions, the adjusting section 111 determines the second and third gains. And the adjusting section 111 instructs the receiving section 103 to amplify the second and third detection signals with the respective gains determined.

The displacement measuring section 112 gets the second and third received echo signals from the receiving section 103 and measures the magnitudes of displacement in the intense and faint echo regions by reference to the second and third received echo signals, respectively. The calculations to be made by the displacement measuring section 112 and the qualitative value calculating section 105 may be performed by the methods disclosed in Patent Document No. 1 and Non-Patent Document No. 1, for example.

By reference to the magnitudes of displacement in the intense and faint echo regions, the qualitative value calculating section 105 calculates the attribute property value in the measuring range of the subject, which may be elasticity, the magnitude of strain, or viscosity, to name a few. For example, by calculating the difference between the magnitudes of displacement of respective displacement measuring points in the intense and faint echo regions, the qualitative value calculating section 105 calculates the magnitude of thickness variation (i.e., the magnitude of strain) between two arbitrary measuring points. Furthermore, the qualitative value calculating section 105 gets information about the subject's highest and lowest blood pressures from the blood pressure value measuring section 108 and calculates the elasticity of the subject's tissue based on that information. The elasticity, magnitude of strain and other qualitative values calculated are output to the image synthesizing section 106.

The tomographic image processing section 104 includes various types of filters, detectors, logarithmic amplifiers, and other components, and analyzes mainly the amplitude of the received echo signal, thereby generating the data of a tomographic image representing the internal structure of the subject as an image. The tomographic image data thus generated is also output to the image synthesizing section 106.

The image synthesizing section 106 superimposes an image representing the two-dimensional distribution of elasticities, which has been generated by the qualitative value calculating section 105, on the tomographic image that has been provided by the tomographic image processing section 104 and gets the resultant synthetic image displayed on the monitor 107. The elasticities that have been obtained by the qualitative value calculating section 105 may be displayed either as they are (i.e., as numerical values) on the monitor 107 or as a graphic representation after having been subjected to statistical processing. Optionally, the display on the monitor 107 may be updated synchronously with the period of deformation of the subject.

Hereinafter, it will be described in further detail exactly how the ultrasonic diagnostic apparatus of this preferred embodiment operates. FIG. 3(a) is a tomographic image representing a carotid arterial vascular wall 200 and its surrounding tissue, which was obtained by the ultrasonic diagnostic apparatus of this preferred embodiment. As shown in FIG. 3(b), this tomographic image was obtained by scanning the measuring range 511 of the subject with m ultrasonic beams 504. On the acoustic line of each of these ultrasonic beams 504, arranged at regular intervals are displacement measuring points 506. As described above, the magnitudes of displacement are calculated at the respective displacement measuring points and the elasticities are calculated based on those magnitudes of displacement.

A number of tomographic images such as the one shown in FIG. 3(a) are usually taken per cardiac cycle of the subject and are updated in real time. Those tomographic images are also called "frames". In the following description, it will be described just as an example how to make measurements on one of the acoustic lines shown in FIG. 3(b).

FIG. 3(c) shows a curve representing the distribution in the depth direction of received echo signal intensities, which were obtained on the acoustic line that is indicated by the dashed line 504 in FIG. 3(a) within their measuring range. In FIG. 3(c), the region identified by the reference numeral 200 is the carotid arterial vascular wall. When the elasticity of the carotid arterial vascular wall is measured, for example, the received echo signals have a very broad intensity distribution on the carotid arterial vascular wall 200. If the measuring range includes such a range with significantly varying echo intensities, first of all, the ultrasonic diagnostic apparatus of this preferred embodiment determines a region with a relatively high echo intensity and a region with a relatively low echo intensity.

For that purpose, the first drive signal is used. Portion (a) of FIG. 4 shows the waveform of the first drive signal 211. Portion (b) of FIG. 4 shows the waveform of the first received echo signal 212, which has been produced by getting the ultrasonic wave reflected from the subject responsive to the first drive signal 211. And portion (c) of FIG. 4 shows the signal intensity 213 of the first received echo signal 212. In these portions of FIG. 4, the abscissa represents the position in the depth direction within the measuring range.

A first detection signal that has been generated by the probe 101 is amplified by the receiving section 103 with a first gain, thereby generating a first received echo signal. That first gain has been determined in advance to be such a value that will not get the maximum amplitude portion of the first received echo signal 212 saturated. And the first received echo signal 212 is stored in the storage section 110.

The adjusting section 111 retrieves the data of the first received echo signal 212 from the storage section 110 and determines, based on the feature quantity of the first received echo signal 212, intense and faint echo regions within a measuring range on the acoustic line of the first received echo signal 212. The feature quantity representing the intensity of the first received echo signal is preferably calculated. For example, either the envelope detection waveform or the logarithmic representation of the first received echo signal may be used as the signal intensity curve 213. Alternatively, the absolute value of the first received echo signal may be obtained and used as the amplitude value as it is.

Next, a threshold value is set based on the maximum amplitude of the first received echo signal, for example. For example, if the maximum value S1 of the signal intensity curve 213 is supposed to be one (unity), one tenth of the maximum value may be set to be the threshold value. And portion of the signal intensity curve that has lower signal intensities than the threshold value may be determined to be the faint echo region 202 within the first received echo signal measuring range. More specifically, displacement measuring points, at which the signal intensities are smaller than the threshold value, are detected and determined to belong to the faint echo region 202. On the other hand, the other portions, at which the signal intensities are equal to or greater than the threshold value, are determined to be the intense echo regions 201. That is to say, displacement measuring points, at which the signal intensities are equal to or greater than the threshold value, are detected and determined to belong to the intense echo region 201. In portion (c) of FIG. 4, the ranges outside of the two intense echo regions 201 are supposed to be out of the measuring range, and therefore, the ranges with low signal intensities outside of the two intense echo regions 201 are not determined to be the faint echo regions 202. The threshold value may be determined based on the average amplitude of the first received echo signal. Alternatively, the average and standard deviation of the amplitudes of the first received echo signal may be calculated and then used to determine the threshold value. Also, the threshold value is preferably determined so that the measuring range includes one intense echo region 201 and one faint echo region 202 to say the least.

Subsequently, based on the feature quantity of the first received echo signal in the intense echo regions 201 (i.e., by reference to the signal intensity curve 213), the second gain is determined. In this case, the second gain is determined so that when the second received echo signal is amplified, the signal does not get saturated in the intense echo regions 201. Specifically, supposing the maximum value of the signal intensity curve 213 in the intense echo regions 201, the second gain, and the saturation level of the receiving section are identified by S1, G2 and Lmax, respectively, G2 is determined so that S1×G2 never exceeds Lmax. For example, S1×G2=0.8× Lmax may be satisfied.

In the same way, based on the feature quantity of the first received echo signal in the faint echo region 202 (i.e., by reference to the signal intensity curve 213), the third gain is determined. In this case, the third gain is determined so that when the third received echo signal is amplified, the signal does not get saturated in the faint echo region 202. Specifically, supposing the maximum value of the signal intensity curve 213 in the faint echo region 202, the third gain, and the saturation level of the receiving section 103 are identified by S2, G3 and Lmax, respectively, G3 is determined so that S3×G3 never exceeds Lmax. For example, S2×G3=0.8× Lmax may be satisfied. In that case, the third gain G3 is greater than the second gain G2.

Then, using the second and third gains that have been set as described above, the second and third drive signals are transmitted to make measurements. Specifically, the second drive signal 221 is generated as shown in portion (a) of FIG. 5 to drive the probe 101. Portion (b) of FIG. 5 shows the waveform of the second received echo signal 222 obtained by amplifying the received signal with the second gain. And portion (c) of FIG. 5 shows the signal intensity curve 223 of the second received echo signal 222. As shown in portion (c) of FIG. 5, the maximum amplitude of the intense echo region 201 is less than 0.8 times as large as the saturation level Lmax of the receiving section 103 and the second received echo signal never gets saturated. This is because the second gain G2 has been determined as described above. As can be seen, the second received echo signal 222 never gets saturated in the intense echo region 201 and has been amplified to have a sufficiently high intensity.

Next, the third drive signal 231 is generated as shown in portion (a) of FIG. 6 to drive the probe 101. Portion (b) of FIG. 6 shows the waveform of the third received echo signal 232 obtained by amplifying the received signal with the third gain. And portion (c) of FIG. 6 shows the signal intensity curve 233 of the third received echo signal 232. As shown in portion (c) of FIG. 6, the maximum amplitude of the faint echo region 202 is less than 0.8 times as large as the saturation level Lmax of the receiving section 103 and the third received echo signal never gets saturated. This is because the third gain G3 has been determined as described above. As can be seen, the third received echo signal 232 never gets saturated in the faint echo region 202 and has been amplified to have a sufficiently high intensity. In this case, in the intense echo region 201, the amplitude has reached the saturation level Lmax of the receiving section 103 and the signal has not been amplified properly. However, since that part of the third received echo signal in the intense echo region 201 is not used for measurement, the measurement would not be affected.

The second and third received echo signals that have been amplified as described above with the second and third gains, respectively, are output to the displacement measuring section 112, which obtains the magnitudes of displacement at the respective displacement measuring points. In this case, the displacement measuring section 112 gets information about the displacement measuring points falling within the intense and faint echo regions 201 and 202 from the adjusting section 111 and uses that information to calculate their magnitudes of displacement. As shown in FIG. 7(a), the second received echo signal 222 is used only to find how much the displacement measuring points falling within the intense echo regions 201 have been displaced. In the same way, the third received echo signal 232 is used only to find how much a displacement measuring point falling within the faint echo region 202 has been displaced as shown in FIG. 7(b). That is to say, as shown in FIG. 7(c), on the same acoustic line 239, only signal parts 222a of the second received echo signal that has been amplified with the second gain G2 are used in the intense echo regions 201 unless those parts 222a fall out of the intense echo regions 201 and only a signal part 232a of the third received echo signal that has been amplified with the third gain G3 is used in the faint echo region 202 unless that part 232a falls out of the faint echo region 202. That is why the results achieved would be as if the received echo signals obtained on the same acoustic line had been amplified with mutually different gains. That is to say, even on the same acoustic line, the received echo signals have been amplified with adequate gains that are never too high to avoid saturation in the regions with high signal intensities, and the received echo signal has been amplified to a sufficiently high level compared to the conventional one in the region with a low signal intensity.

That is why the magnitudes of displacement can be measured with almost the same degree of accuracy in both a region with a relatively high signal intensity and a region with a relatively low signal intensity. As a result, even though the magnitude of displacement cannot be measured so accurately according to a conventional technique in a region where the received echo signal has a relatively low intensity, the magnitude of displacement in such a region can also be measured highly accurately according to the present invention.

Also, when attention is paid to each specific displacement measuring point, the magnitude of displacement is calculated using only the second received echo signal or the third received echo signal without changing the signals halfway one into the other. For that reason, the magnitude of displacement can be calculated correctly.

As described above, ultrasonic measurements are made several times per cardiac cycle. That is why the procedure described above needs to be performed a number of times. Nevertheless, as the signal intensity of a received echo signal depends on whether or not any difference has been made on the subject's tissue, the signal intensity obtained during the measurements will not vary significantly. That is to say, in a measuring range where the signal intensity should be low, the signal intensity is almost always low and never varies significantly. For that reason, once the intense echo region 201 and the faint echo region 202 have been determined and once the second and third gains have been determined, the received echo signals can always be amplified with the same values whenever measurement is made after that. Consequently, the procedure of determining the intense and faint echo regions 201 and 202 and the second and third gains using the first drive signal has only to be done once (or a few times at most) in a cardiac cycle. As such a procedure may be carried out synchronously with a cardiac cycle, the intense and faint echo regions 201 and 202 and the second and third gains could be determined once in several cardiac cycles, too.

FIG. 8 is a timing diagram showing the drive waveform of a transmitted signal and its associated gains for use in the receiving section 103 in a situation where the first drive signal is transmitted only once in a cardiac cycle. If one cardiac cycle is determined using the R wave 251 of the electrocardiogram as a trigger, the first drive signal 211 is generated once as soon as the R wave 251 has been detected and the first received echo signal is obtained with a predetermined gain G1, thereby determining the intense echo region 201 and the faint echo region 202. Meanwhile, the second and third gains G2 and G3 are also determined. After that, second and third drive signals 221 and 231 are generated and second and third detection signals are respectively amplified with the second and third gains G2 and G3 that have been determined, thereby generating second and third received echo signals. If measurements need to be made on the same acoustic line after that, only the second and third drive signals 221 and 231 may be transmitted repeatedly and the second and third received echo signals 222 and 232 may be generated with the second and third gains G2 and G3 that have been determined at the beginning. And when the R wave 251 is received next time, the first drive signal 211 will be generated again to determine the intense and faint echo regions 201 and 202 and second and third gains for use in that cardiac cycle.

In the example described above, the measurements are supposed to be made on a single acoustic line. Next, it will be described when to apply the drive signal in a situation where measurements are carried out two-dimensionally.

First of all, suppose the measurements are done for n frames in one cardiac cycle as shown in FIG. 9(a). In that case, in each of those frames, the subject's measuring range 511 is scanned with m ultrasonic beams as shown in FIG. 9(b). Specifically, in the first frame of one cardiac cycle, the first drive signal needs to be transmitted to determine the intense and faint echo regions 201 and 202 and second and third gains as described above. As shown in FIG. 9(b), the first drive signal 211 is transmitted m times to scan the measuring range, thereby determining the intense and faint echo regions 201 and 202 and second and third gains on each of the first through $m^{th}$ acoustic lines. Next, the second drive signal is transmitted m times to scan the measuring range, thereby amplifying the second detection signal obtained on each acoustic line with the second gain and obtaining the second received echo signal. Thereafter, the third drive signal is transmitted m times to scan the measuring range, thereby amplifying the third detection signal obtained on each acoustic line with the third gain and obtaining the third received echo signal. In this manner, measurement is done on the first frame. In the remaining second through $n^{th}$ frames, the second and third drive signals are transmitted as described above and the second and third received echo signals are obtained using the second and third gains that have been determined in the first frame.

The displacement measuring section 112 measures the magnitudes of displacement of respective displacement measuring points on each acoustic line by using the second and third received echo signals on an acoustic line basis as described above. In this manner, the magnitudes of displacement in the measuring range can be obtained two-dimensionally. As a result, an image representing the two-dimensional distribution of elasticities can be generated.

By determining the intense and faint echo regions 201 and 202 and the second and third gains on an acoustic line basis as described above, measurements could be done accurately overall in the entire measuring range even if the subject' tissue were not uniform perpendicularly to the acoustic lines. Stated otherwise, if it is already known that the subject's tissue is uniform perpendicularly to the acoustic lines (e.g., if the given tomographic image clearly indicates that the carotid artery runs substantially parallel to the skin), the intense and faint echo regions 201 and 202 and the second and third gains do not have to be determined on all acoustic lines. Alternatively, in that case, the intense and faint echo regions 201 and 202 and the second and third gains may be determined only on some acoustic lines that have been selected at regular intervals, and measurements on the other non-selected acoustic lines may be carried out using the intense and faint echo regions 201 and 202 and the second and third gains that have been determined for an adjacent acoustic line.

As described above, according to the present invention, intense and faint echo regions, in which the received echo signal has relatively high and relatively low signal intensities, are defined within a measuring range on the subject by using the first received echo signal responsive to the first drive signal, and the second and third gains are determined based on the feature quantity about the signal intensities of the first received echo signal in the intense and faint echo regions. The second and third received echo signals, which have been amplified with the second and third gains determined, have been maximized as far as the signal intensities in the intense and faint echo regions are not saturated. That is why by calculating the magnitude of displacement and an attribute property value by using the second and third received echo signals for the intense and faint echo regions, respectively, almost equally accurate results of measurement can be obtained over the entire measuring range. Consequently, if the measuring range on the subject includes an arterial vascular wall, the magnitude of displacement can be obtained even in an intima-media region and its surrounding tissue with a relatively low received echo signal intensity almost as accurately as in the other region with a relatively high received echo signal intensity.

In the preferred embodiment described above, the adjusting section 111 determines the second and third gains based on the first received echo signal. However, as indicated by the dotted arrow in FIG. 1, the adjusting section 111 may adjust not only the drive signal that the transmitting section 102 is going to output but also the intensity of an ultrasonic wave that the probe 101 has sent out.

For example, first of all, the first drive signal 211' is generated as shown in FIG. 10(a), and the intense and faint echo regions 201 and 202 are determined based on the feature quantity about the signal intensity of the first received echo signal as described above. Next, based on the feature quantities about the signal intensities of the first received echo signal in the intense and faint echo regions 201 and 202, the intensity of the ultrasonic wave to transmit may be changed so as to maximize the signal components of the second and third received echo signals in the intense and faint echo regions 201 and 202, respectively, as far as the signal does not get saturated in the receiving section 103. For that purpose, the intensity of the ultrasonic wave to transmit may be changed either by adjusting the amplitudes w1 and w2 of the second and third drive signals 221' and 231' as shown in FIG. 10(a) or by changing the amplitude or wave number of pulses with the amplitude w1 of the second and third drive signals 221" and 231" kept constant as shown in FIG. 10(b). Nevertheless, if the number of waves were too many, the resolution would decrease. For that reason, the number of waves of pulses is preferably determined by the precision of measurement required.

Also, in the preferred embodiment described above, the receiving section 103 includes only one gain control amplifier 103b. But the receiving section 103 may include two or more gain control amplifiers as well. FIG. 2(b) is a block diagram illustrating an alternative configuration for the receiving section 103. As shown in FIG. 2(b), this receiving section 103 includes a preamplifier 103a, gain control amplifiers #1 103d and #2 103e, and A/D converters #1 103g and #2 103f. The signal that has been amplified by the preamplifier 103a is input first to gain control amplifier #1 103d with a gain g1, the output of which is then passed to gain control amplifier #2 103e with a gain g2. These gains are controlled by the adjusting section 111 so that the first gain g1 is equal to the second gain G2 and that the product of the gains g1 and g2 is equal to the third gain G3. The second detection signal is amplified by gain control amplifier #1 with the gain g1 (that is equal to the second gain G2) and then converted into a digital signal by A/D converter #1 103g. On the other hand, the third detection signal is amplified by gain control amplifier #1 with the gain g1, further amplified by gain control amplifier #2 with the gain g2, and then converted into a digital signal by A/D converter #2 103f. According to such a configuration, the received echo signals in the intense and faint echo regions 201 and 202 can be digitized by two separate A/D converters, and therefore, the dynamic range can be expanded.

Furthermore, in the preferred embodiment described above, the second and third received echo signals responding to the second and third drive signals are used to make measurements on the intense and faint echo regions, respectively. However, the combinations may also be made the other way around. That is to say, the second received echo signal could be used to make measurement on the faint echo region and the third received echo signal could be used to make measurement on the intense echo region. In that case, the second gain should be greater than the third gain. Likewise, the second and third drive signals do not always have to be transmitted in this order, but the third drive signal could be transmitted earlier than the second drive signal, too.

Furthermore, in the preferred embodiment described above, based on the feature quantity about the signal intensity of the first received echo signal, the measuring range is supposed to be split into the intense and faint echo regions. However, the measuring range could also be divided into three or more regions. For example, if the measuring range needs to be divided into three regions, then two threshold values are set based on the feature quantity about the signal intensity of the first received echo signal, and intense, moderate and faint echo regions are defined within the measuring range on an acoustic line by using those two threshold values. And based on the feature quantities about the signal intensities of the first received echo signal in those three regions defined, second, third and fourth gains G2, G3 and G4 are determined. Furthermore, second, third and fourth drive signals are generated and applied to get second, third and fourth detection signals, respectively, which are then amplified with the second, third and fourth gains G2, G3 and G4, respectively, thereby obtaining second, third and fourth received echo signals. In that case, the displacement measuring section can measure the magnitudes of displacement at respective displacement measuring points in the intense, moderate and faint echo regions based on the second, third and fourth received echo signals, respectively.

Furthermore, in the preferred embodiment described above, the number of received signals for use to obtain data of one frame agrees with the number of divided regions defined in the measuring range. Specifically, in the preferred embodiment described above, the measuring range is split into two echo regions and data of one frame is obtained using the second and third received echo signals. However, the number of received echo signals to make up one frame may be greater than the number of divided regions that form the measuring range. For example, the intense and faint echo regions may be defined in the measuring range and data of one frame may be made up of three or more received signals. More specifically, even when the intense and faint echo regions are defined in the measuring range as in the preferred embodiment described above, data of one frame may also be obtained by using second, third and fourth received echo signals responding to second, third and fourth drive signals, respectively. In that case, the second received echo signal is amplified with the second gain, and the third and fourth received echo signals are amplified with the third gain. Also, the magnitude of displacement in the intense echo region is measured using the second received echo signal and the magnitude of displacement in the faint echo region is measured using the third and fourth received echo signals. If the two magnitudes of displacement that have been calculated for the faint echo region using the third and fourth received echo signals, respectively, have their average calculated and used as the magnitude of displacement in the faint echo region, the influence of noise can be reduced significantly.

As can be seen, the magnitude of displacement in the same kind of echo region may be measured using the same gain but two or more received echo signals. That is to say, the ultrasonic diagnostic apparatus of the present invention may transmit N different (where N is an integer that is equal to or greater than three) drive signals, including a first drive signal, generate a first received echo signal and (N−1) received echo signals, and divide the measuring range into M different kinds (where M is an integer that falls within the range of 2 to N−1) of echo regions.

Furthermore, in the preferred embodiment described above, the subject is supposed to be deformed actively due to his or her heartbeat. However, the ultrasonic diagnostic apparatus of the present invention can also measure highly accurately an attribute property (such as the elasticity) of even a non-actively-deformable tissue such as a static organ. FIG. 11 schematically illustrates an arrangement for measuring the elasticity of a static organ. If the subject 351 includes a static organ 352 such as a liver, a vibrator 310 is used to deform the static organ 352 periodically. The vibrator 310 includes an arm 300 with a contact portion 302 to contact with the subject 351 and a drive section 304. As indicated by the arrow, the arm 300 is vibrated in a predetermined period by the drive section 304. If the arm 300 is vibrated with the contact portion 302 brought into contact with the subject, the subject can be deformed periodically.

When the elasticity of the static organ 352 is measured, the probe 101 transmits and receives ultrasonic waves, while the static organ 352 of the subject 351 is periodically pressured and relaxed by the vibrator 310. In this case, the vibrator 310 outputs a trigger signal to the storage section 110, the adjusting section 111, the qualitative value calculating section 105 and the image synthesizing section 106 synchronously with one period of vibration, thereby getting the measurement done as described above. As a result, the thickness variation (i.e., the magnitude of strain) between the measuring points that have been set in the static organ 352 can be measured. In addition, the difference between the pressures applied to the subject 351 due to the vibrations produced by the vibrator 310 can also be obtained. As a result, the elasticity can be calculated based on the magnitudes of the thickness variation and the pressure difference.

If the vibrator 310 is used in this manner, the elasticity of a non-living subject can also be measured. For example, the elasticity of an elastic tube may be measured to determine how much the tube has deteriorated.

INDUSTRIAL APPLICABILITY

An ultrasonic diagnostic apparatus according to the present invention can be used effectively to measure an internal qualitative value of a subject. Among other things, the present invention can be used particularly effectively to measure highly accurately a qualitative value of a subject that includes portions with quite different echo intensities.

REFERENCE SIGNS LIST 100 control section
101 probe
102 transmitting section
103 receiving section
104 tomographic image processing section
105 qualitative value calculating section
106 image synthesizing section
107 monitor
108 blood pressure value measuring section
109 sync signal detecting section
110 storage section
111 adjusting section
112 displacement measuring section
210 subject
212 static organ
300 arm
302 contact portion
304 drive section
310 vibrator

The invention claimed is:

1. An ultrasonic diagnostic apparatus comprising:
a transmitting microcomputer configured to generate N different drive signals, where N is an integer that is equal to or greater than three, including a first drive signal, to drive a probe that sends out ultrasonic waves toward a subject;
a receiving microcomputer configured to receive echoes, which have been produced as a result of reflection of the ultrasonic waves from the subject in response to the N different drive signals, received by the probe and amplifying the respective signals generated, thereby generating a first received echo signal that responds to the first drive signal and N−1 received echo signals;
a computer readable storage medium that stores the first received echo signal;
an adjusting microcomputer configured to define M different echo regions, where M is an integer that falls within the range of two through N−1, within a measuring range on the acoustic line of the first received echo signal based on a feature quantity of the first received echo signal that is stored in the computer readable storage medium and for determining either the amplification gain to generate the N−1 received echo signals in the receiving microcomputer or the waveforms of the N−1 different drive signals, except the first drive signal, based on the feature quantities of the first received echo signal in the M different echo regions; and
a displacement measuring microcomputer configured to measure section for measuring the respective magnitudes of displacement in the M different echo regions based on the N−1 received echo signals.

2. The ultrasonic diagnostic apparatus of claim 1, wherein N−1 and M are both equal to two;
wherein the M different echo regions are an intense echo region in which the echo signal has a first intensity and a faint echo region in which the echo signal has a second intensity, wherein the first intensity is higher than the second intensity;
wherein the transmitting microcomputer generates not only the first drive signal but also second and third drive signals as well;
wherein the receiving microcomputer receives echoes, which have been produced as a result of reflection of the ultrasonic waves from the subject in response to the first, second and third drive signals, received by the probe and amplifies the respective signals generated with first, second and third gains, respectively, thereby generating the first received echo signal and second and third received echo signals;
wherein the adjusting microcomputer defines the intense and faint echo regions within the measuring range on the acoustic line of the first received echo signal based on the feature quantity of the first received echo signal that is stored in the storage medium and determines the second and third gains based on the feature quantities of the first received echo signal in the intense and faint echo regions and
wherein the displacement measuring microcomputer measures the respective magnitudes of displacement in the intense and faint echo regions based on the second and third received echo signals, respectively.

3. The ultrasonic diagnostic apparatus of claim 2, wherein the adjusting microcomputer determines the gains for the intense and faint echo regions by the amplitude value of the first received echo signal so that the maximum amplitudes of the second and third received echo signals in the intense and faint echo regions, respectively, fall within a predetermined range.

4. The ultrasonic diagnostic apparatus of claim 3, wherein the adjusting microcomputer is configured to determine the feature quantity of the first received echo signal to be the amplitude of the first received echo signal.

5. The ultrasonic diagnostic apparatus of claim 4, wherein the adjusting microcomputer defines a region in which the amplitude of the first received echo signal is equal to or greater than a predetermined threshold value to be the intense echo region.

6. The ultrasonic diagnostic apparatus of claim 5, wherein the adjusting microcomputer defines a region in which the amplitude of the first received echo signal is smaller than the predetermined threshold value to be the faint echo region.

7. The ultrasonic diagnostic apparatus of claim 6, wherein the adjusting microcomputer is configured to determine the threshold value based on the maximum amplitude of the first received echo signal.

8. The ultrasonic diagnostic apparatus of claim 6, wherein the adjusting microcomputer is configured to determine the threshold value based on the average amplitude of the first received echo signal.

9. The ultrasonic diagnostic apparatus of claim 6, wherein the adjusting microcomputer is configured to determine the threshold value based on the average amplitude and standard deviation of the first received echo signal.

10. The ultrasonic diagnostic apparatus of claim 2, wherein the adjusting microcomputer determines the gains for the intense and faint echo regions synchronously with one cardiac cycle of the subject.

11. The ultrasonic diagnostic apparatus of claim 10, wherein the adjusting microcomputer receives information about the cardiac cycle from either an electrocardiograph or phonocardiograph that is connected to the subject.

12. The ultrasonic diagnostic apparatus of claim 2, wherein the adjusting microcomputer keeps the second and third gains constant within the same deformation period of the subject.

13. The ultrasonic diagnostic apparatus of claim 2, wherein the transmitting microcomputer sets multiple acoustic lines on the subject and the transmitting microcomputer generates the first, second and third drive signals so that the ultrasonic waves scan the subject on their associated acoustic lines, and
wherein the receiving microcomputer generates multiple sets of first, second and third received echo signals on the multiple acoustic lines, and
wherein the storage medium stores the respective first received echo signals of the multiple sets.

14. The ultrasonic diagnostic apparatus of claim 2, further comprising a qualitative value calculating microcomputer configured to calculate the attribute property value of the subject within the measuring range based on the respective magnitudes of displacement in the M different echo regions.

15. The ultrasonic diagnostic apparatus of claim 14, wherein the qualitative value calculating microcomputer is configured to determine a magnitude of strain as the attribute property.

16. The ultrasonic diagnostic apparatus of claim 14, wherein the qualitative value calculating microcomputer is configured to determine a modulus of elasticity as the attribute property.

17. The ultrasonic diagnostic apparatus of claim 14, wherein the qualitative value calculating microcomputer calculates the attribute property value of the subject within the measuring range based on the respective magnitudes of displacement in the intense and faint echo regions.

18. The ultrasonic diagnostic apparatus of claim 17, wherein the qualitative value calculating microcomputer is configured to determine a magnitude of strain as the attribute property.

19. The ultrasonic diagnostic apparatus of claim 17, wherein the qualitative value calculating microcomputer is configured to determine a modulus of elasticity as the attribute property.

20. The ultrasonic diagnostic apparatus of claim 1, wherein N−1 and M are both equal to two;
wherein the M different echo regions are an intense echo region in which the echo signal has a first intensity and a faint echo region in which the echo signal has a second intensity, wherein the first intensity is higher than the second intensity;
wherein the transmitting microcomputer generates not only the first drive signal but also second and third drive signals as well;
wherein the receiving microcomputer receives echoes, which have been produced as a result of reflection of the ultrasonic waves from the subject in response to the first, second and third drive signals, received by the probe and amplifies the respective signals generated, thereby generating the first received echo signal and second and third received echo signals;
wherein the adjusting microcomputer defines the intense and faint echo regions within the measuring range on the acoustic line of the first received echo signal based on the feature quantity of the first received echo signal that is stored in the storage medium and determines the waveforms of the second and third drive signals in the transmitting microcomputer based on the feature quantities of the first received echo signal in the intense and faint echo regions, and
wherein the displacement measuring microcomputer measures the respective magnitudes of displacement in the intense and faint echo regions based on the second and third received echo signals, respectively.

21. The ultrasonic diagnostic apparatus of claim 20, wherein the adjusting microcomputer determines the waveforms of the second and third drive signals by the amplitude value of the first echo signal so that the maximum amplitudes of the second and third received echo signals in the intense and faint echo regions, respectively, fall within a predetermined range.

22. The ultrasonic diagnostic apparatus of claim 20, wherein the adjusting microcomputer adjusts the amplitude value of the drive signal.

23. The ultrasonic diagnostic apparatus of claim 20, wherein the adjusting microcomputer determines the waveforms of the second and third drive signals synchronously with one cardiac cycle of the subject.

24. The ultrasonic diagnostic apparatus of claim 20, wherein the adjusting microcomputer keeps the waveforms of the second and third drive signals constant through the same deformation period of the subject.

25. The ultrasonic diagnostic apparatus of claim 20, further comprising a qualitative value calculating microcomputer configured to calculate the attribute property value of the subject within the measuring range based on the respective magnitudes of displacement in the M different echo regions.

26. The ultrasonic diagnostic apparatus of claim 25, wherein the qualitative value calculating microcomputer calculates the attribute property value of the subject within the measuring range based on the respective magnitudes of displacement in the intense and faint echo regions.

27. The ultrasonic diagnostic apparatus of claim 26, wherein the qualitative value calculating microcomputer is configured to determine a magnitude of strain as the attribute property.

28. The ultrasonic diagnostic apparatus of claim 26, wherein the qualitative value calculating microcomputer is configured to determine a modulus of elasticity as the attribute property.

29. The ultrasonic diagnostic apparatus of claim 25, wherein the qualitative value calculating microcomputer is configured to determine a magnitude of strain as the attribute property.

30. The ultrasonic diagnostic apparatus of claim 25, wherein the qualitative value calculating microcomputer is configured to determine a modulus of elasticity as the attribute property.

31. The ultrasonic diagnostic apparatus of claim 1, wherein at least a portion of the subject is deformed periodically by a vibrator and wherein the adjusting microcomputer receives information about the period of deformation from the vibrator.

* * * * *